(12) United States Patent
Main et al.

US007656998B2

(10) Patent No.: US 7,656,998 B2
(45) Date of Patent: Feb. 2, 2010

(54) UNIFIED QUALITY ASSURANCE FOR A RADIATION TREATMENT DELIVERY SYSTEM

(75) Inventors: William T. Main, Aptos, CA (US); Eric Earnst, Saratoga, CA (US); Gopinath Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 117 days.

(21) Appl. No.: 11/273,711

(22) Filed: Nov. 14, 2005

(65) Prior Publication Data

US 2007/0127622 A1 Jun. 7, 2007

(51) Int. Cl.
*A61N 5/10* (2006.01)
(52) U.S. Cl. ............... 378/65; 378/9; 378/19; 378/196; 378/197; 378/198; 600/427
(58) Field of Classification Search ......... 600/407, 600/424, 426, 427, 429; 73/1.01, 114.47; 378/65, 207, 209, 4, 8, 9, 11, 19, 20, 64, 378/195–198; 250/252.1; 702/8, 94, 150, 702/152
See application file for complete search history.

(56) References Cited

U.S. PATENT DOCUMENTS

| | | | |
|---|---|---|---|
| 1,252,550 | A | 1/1918 | Champney |
| 6,501,981 | B1 * | 12/2002 | Schweikard et al. ........ 600/427 |
| 6,528,803 | B1 | 3/2003 | Ritt |
| 6,675,116 | B1 | 1/2004 | Ritt |
| 6,842,502 | B2 | 1/2005 | Jaffray et al. |
| 7,187,792 | B2 * | 3/2007 | Fu et al. ..................... 382/128 |
| 2004/0158146 | A1 * | 8/2004 | Mate et al. .................. 600/427 |
| 2005/0080332 | A1 | 4/2005 | Shiu et al. |
| 2005/0234327 | A1 * | 10/2005 | Saracen et al. .............. 600/407 |
| 2007/0071176 | A1 | 3/2007 | Main et al. |

OTHER PUBLICATIONS

"Dynamic Phantom," CIRS Model 008 Dynamic Thorax Phantom Specifications, pp. 53-54.
"Anthropomorphic Phantoms," Radiological Physics Center. Retrieved from http://rpc.mdanderson.org/rpc/services/Anthropomorphic_%20Phantoms/Anth_SRS.htm (Retrieved on Mar. 28, 2007).
"Instructions for SRS Quality Audit System," Radiological Physics Center. Retrieved from http://rpc.mdanderson.org/rpc/services/Anthropomorphic_%20Phantoms/SRSInstrucForInst.pdf (Retrieved on Mar. 28, 2007).
Yu, Cheng Ph.D. et al., "An Anthropomorphic Phantom Study of the Accuracy of CyberKnife Spinal Radiosurgery," Neurosurgery, vol. 55, No. 5, Nov. 2004, pp. 1138-1149.
PCT International Search Report, PCT/US06/44253 filed Nov. 13, 2006, mailed Jan. 10, 2008.
PCT Written Opinion of the International Searching Authority, PCT/US06/44253 filed Nov. 13, 2006, mailed Jan. 10, 2008.

* cited by examiner

*Primary Examiner*—Brian Casler
*Assistant Examiner*—Elmer Chao
(74) *Attorney, Agent, or Firm*—Blakely, Sokoloff, Taylor & Zafman LLP (57) ABSTRACT

A unified quality assurance technique to verify alignment of a radiation treatment delivery system. In one embodiment, a radiation treatment source is instructed to move to a preset source position. An image of the radiation treatment source at its actual source position is generated and compared against a reference image to determine whether the radiation treatment source correctly achieved the preset source position. In one embodiment, a positioning system is instructed to move a target detector to a preset target position. An image of the target detector at its actual target position is generated and compared against a reference target image to determine whether the positioning system correctly achieved the preset target position.

26 Claims, 6 Drawing Sheets

QA TEST #5

FIG. 4

QA TEST #6

UNIFIED QUALITY ASSURANCE FOR A RADIATION TREATMENT DELIVERY SYSTEM

TECHNICAL FIELD

This disclosure relates generally to quality assurance for radiation treatment delivery systems.

BACKGROUND

In radiosurgery or radiotherapy (collectively referred to as radiation treatment) very intense and precisely collimated doses of radiation are delivered to a target region in the body of a patient in order to treat or destroy lesions. Typically, the target region consists of a volume of tumorous tissue. Radiation treatment requires an extremely accurate spatial localization of the targeted lesions. Radiation treatment offers apparent advantages over conventional surgery, during which a surgeon's scalpel removes the lesion, by avoiding the common risks and problems associated with open surgery. These problems include invasiveness, high costs, the need for in-hospital stays and general anesthesia, and complications associated with post-operative recovery. When a lesion is located close to critical organs, nerves, or arteries, the risks of conventional surgery are even greater.

As a first step in performing radiation treatment, it is necessary to determine with great precision the location of a lesion and any surrounding critical structures, relative to the reference frame of the treatment device. Computed tomography ("CT"), magnetic resonance imaging ("MRI") scans, and other imaging modalities enable practitioners to precisely locate a lesion relative to skeletal landmarks or implanted fiducial markers. However, it is also necessary to control the position of the radiation source so that its beam can be precisely directed to the target tissue while avoiding adjacent critical body structures.

Thus radiation treatment necessitates high precision diagnosis and high precision radiation source control. The consequences of deviating outside the prescribed tolerances for the diagnosis and the radiation source control can be potentially devastating to a patient. Accordingly, quality assurance mechanisms should be integrated into a radiation treatment delivery system to ensure proper alignment and configuration of the system prior to delivering a prescribed radiation dose to a patient.

Conventional quality assurance mechanisms include pointing the radiation source at an alignment marker, delivering a radiation dose to the alignment marker, and then analyzing the alignment marker itself to determine if the prescribed dose was actually delivered to the correct location. If the prescribed dose was delivered as expected, then the radiation treatment delivery system is deemed properly aligned. If the prescribed dose was not delivered as expected, then the radiation treatment delivery system is deemed misaligned. Conventional alignment markers include silver loaded gels capsules or photographic film canisters that can store readable information about the distribution of the radiation dose delivered to the alignment marker. However, extracting this alignment information from silver loaded gels or photographic film canisters located within the alignment marker itself is a time consuming and costly task.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a system and method for unified quality assurance of an image guided radiation treatment delivery system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
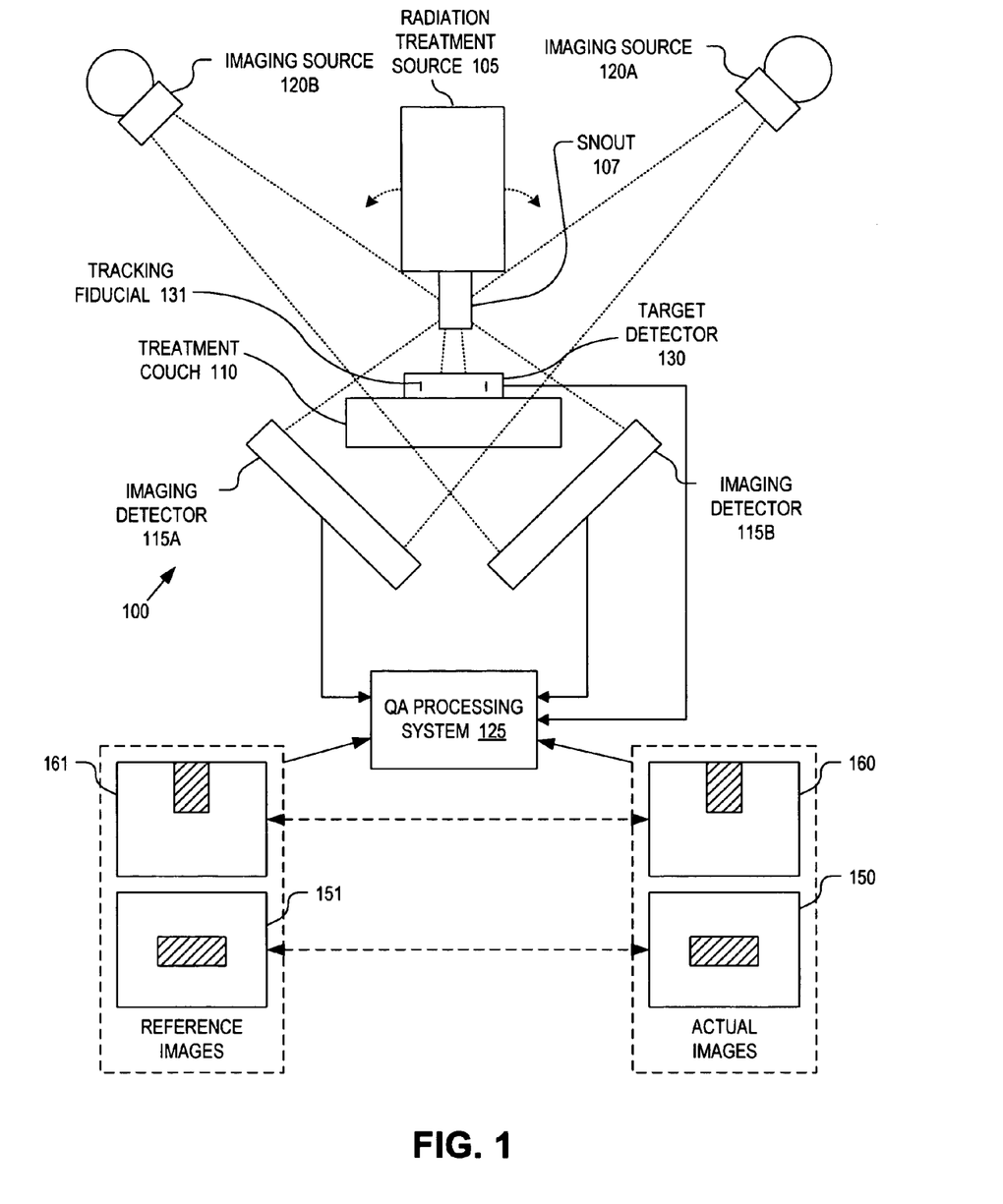
FIG. 1 is block diagram illustrating execution of a unified quality assurance confidence check on a radiation treatment delivery system, in accordance with an embodiment of the invention.

FIG. 1 is block diagram illustrating execution of a unified quality assurance confidence check on a radiation treatment delivery system 100, in accordance with an embodiment of the invention. The illustrated embodiment of radiation treatment delivery system 100 includes a radiation treatment source 105, a treatment couch 110, imaging detectors 115A and 115B (collectively 115, also referred to as imagers), and imaging sources 120A and 120B (collectively 120). Radiation treatment delivery system 100 further includes a quality assurance ("QA") subsystem that includes a QA processing system 125 for analyzing exposure images and/or calculating delivered radiation doses and a target detector 130.

System 100 may be used to perform radiotherapy or radiosurgery to treat or destroy lesions within a patient. During radiation treatment, the patient rests on treatment couch 110, which is maneuvered to position the lesion or volume of interest ("VOI") to a preset position or within an operating range accessible to radiation treatment source 105 (e.g., field of view). Similarly, radiation treatment source 105 is maneuvered with multiple degrees of freedom (e.g., rotational and translational freedom) to one or more locations during delivery of a treatment plan. At each location, radiation treatment source 105 delivers a dose of radiation as prescribed by the treatment plan.

In one embodiment, radiation treatment delivery system 100 is an image guided radiation treatment delivery system. Together, imaging sources 120 and imaging detectors 115 form an image guidance system that provides visual control over the position of treatment couch 110 and the patient thereon. In one embodiment, treatment couch 110 may be coupled to a couch positioning system (e.g., see FIG. 7) that receives feedback from the image guidance system to provide accurate control over both the displacement and orientation of the VOI within the patient. In one embodiment, visual feedback from the image guidance system is further used to position and align radiation treatment source 105 with the target VOI within the patient.

Prior to delivery of the treatment plan to a patient, it is important to execute quality assurance ("QA") mechanisms to ensure radiation treatment delivery system 100 is properly aligned and configured. These QA mechanisms, also referred to as confidence checks, validate that the image guidance system, the couch positioning system (see FIG. 7), the source positioning system (see FIG. 7), and radiation treatment source 105, itself, are all calibrated and aligned with each other. If anyone of these subsystems is misaligned with one or more other subsystems, a treatment plan could be erroneously delivered to a patient's detriment.

In the illustrated embodiment of FIG. 1, target detector 130 is supported on treatment couch 110. Target detector 130 may be temporarily placed onto treatment couch 130 during QA testing. In one embodiment, target detector 130 may even be built into treatment couch 110. By using treatment couch 110 to support target detector 130, target detector 130 may be used to validate the ability of the couch positioning system (e.g., robotic couch arm 3013 illustrated in FIG. 7) to accurately maneuver treatment couch 110 and position target detector 130 to a preset target position.

In one embodiment, target detector 130 may be a shadow phantom or QA marker that includes tracking fiducials 131. The imaging system uses tracking fiducials 131 to visually lock onto the position of target detector 130 and provide position/orientation feedback information to the couch positioning system and/or source positioning system. In one embodiment, tracking fiducials 131 are metallic wires embedded within or on target detector 130. In one embodiment, target detector 130 may be fabricated into the shape of a human head and placed on a headrest of the treatment couch 110. In this human head embodiment, tracking fiducials 131 may represent skeletal structure(s) that can be visually locked onto by the image guidance system (e.g., using X-rays emitted from imaging sources 120).

QA processing system 125 is communicatively coupled to target detector 130 (e.g., wired or wireless link) to receive QA data therefrom. QA processing system 125 may receive exposure images generated in response to a dose of radiation being delivered to target detector 130 from radiation treatment source 105. QA processing system 125 may then analyze the exposure images to determine whether radiation treatment delivery system 100 is aligned and calibrated (discussed in detail in connection with FIG. 3). In one embodiment, target detector 130 may be implemented using the IMRTlog sensor from Cardinal Health, Inc. of Dublin Ohio or the Mapcheck two dimensional detector by Sun Nuclear, Corp. of Melbourne, Fla. These detectors provide real-time feedback to QA processing system 125. Other radiation detecting equipment may be used as well. In other embodiments, target detector 130 is a housing supporting radiographic film that generates an exposure image in response to the dose of radiation from radiation treatment source 105. This radiographic film may then be analyzed by QA processing system 125 to determine whether radiation treatment delivery system 100 is aligned.

In one embodiment, QA processing system 125 may further be coupled to imaging detectors 115 to receive additional QA data therefrom. QA processing system 125 may receive exposure images generated in response to imaging sources 120. The exposure images generated by the image guidance system may include images taken of a portion of radiation treatment source 105 (e.g., snout 107, one or more calibration targets mounted to radiation treatment source 105, or the like) and/or images taken of target detector 130 itself. These images of the actual source position of radiation treatment source 105 and the actual target position of target detector 130 may then be compared against reference source images and reference target images to determine whether radiation treatment delivery system 100 is aligned and calibrated (discussed in detail in connection with FIG. 3).

QA processing system 125 may be a stand alone machine dedicated for QA analysis or integrated into other control systems of radiation treatment delivery system 100. Furthermore, although QA processing system 125 is illustrated as a single entity, it should be appreciated that FIG. 1 is a functional block diagram, and as such, QA processing system 125 may represent multiple distinct machines. QA processing system 125 represents an image processing system for analyzing exposure images and/or a dose processing system for analyzing a dose of radiation delivered by radiation treatment source 105.

Figure 2:
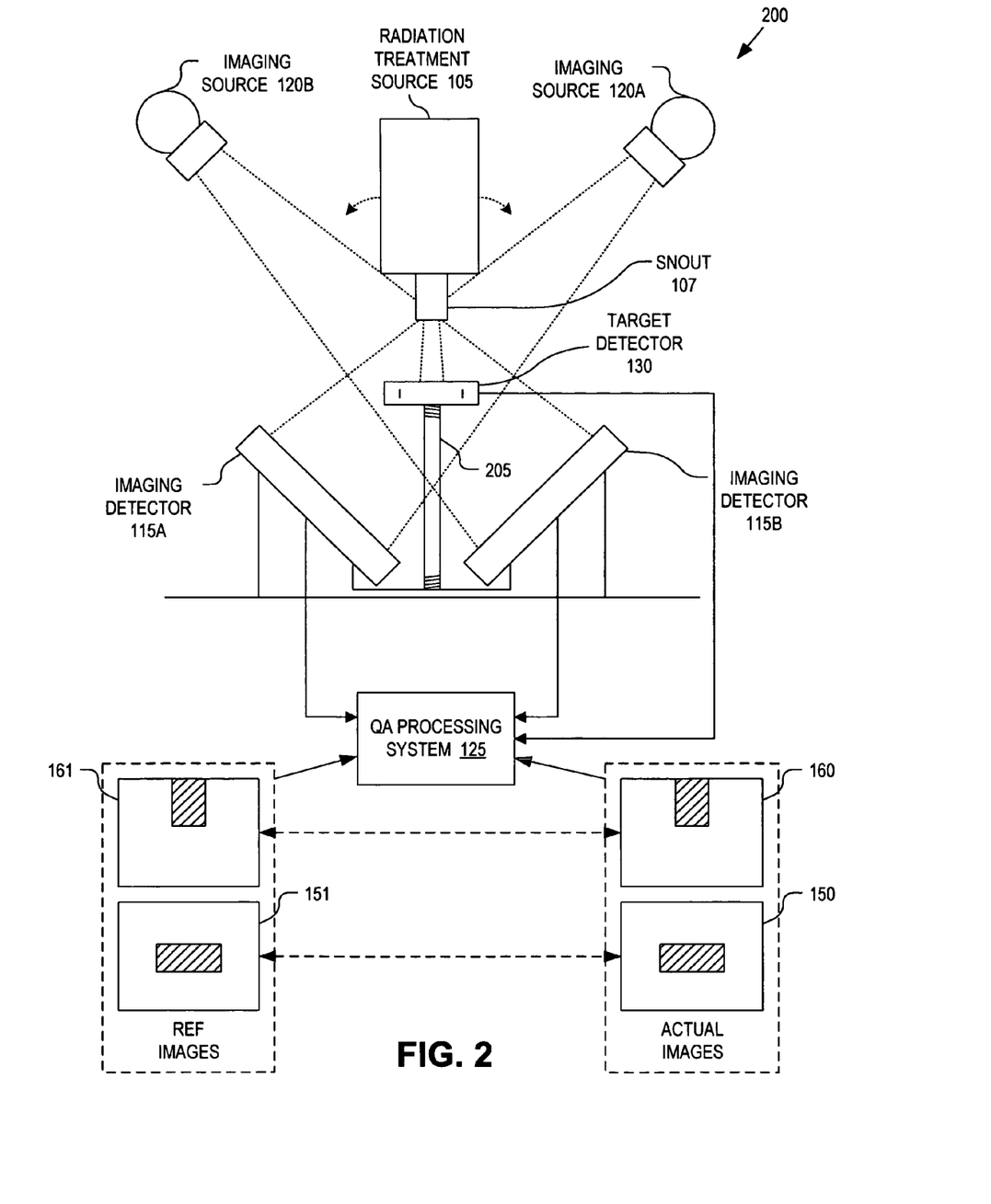
FIG. 2 is block diagram illustrating execution of a unified quality assurance confidence check on a radiation treatment delivery system, in accordance with an embodiment of the invention.

FIG. 2 is block diagram illustrating execution of a unified QA confidence check on a radiation treatment delivery system 200, in accordance with an embodiment of the invention. Radiation treatment delivery system 200 is similar to radiation treatment delivery system 100, except QA confidence checks are performed with treatment couch 110 moved off to the side or out of the way, and target detector 130 positioned at a known, fixed reference point. In the illustrated embodiment, target detector 130 is stationed at the known, fixed reference point using an iso-post 205. In one embodiment, iso-post 205 is a ridged support that positions target detector 130 at an imaging center of the image guidance system. It should be appreciated that any ridged support may be used to station target detector 130 at the known, fixed reference point.

With target detector 130 positioned at the known, fixed reference point, images of target detector 130 may be captured and compared against reference images of target detector 130 to determine whether the image guidance system is aligned. Additionally, target detector 130 may be exposed to a dose of radiation from radiation treatment source 105 and the exposure image compared to a reference exposure image to determine whether the source positioning system is aligned and functioning as expected. Furthermore, the exposure image generated in response to the dose of radiation may be further analyzed to determine whether an expected dose was actually delivered, thereby validating radiation treatment source 105 itself. A unified QA process, which includes the above mentioned QA techniques, is discussed below.

Figure 3:
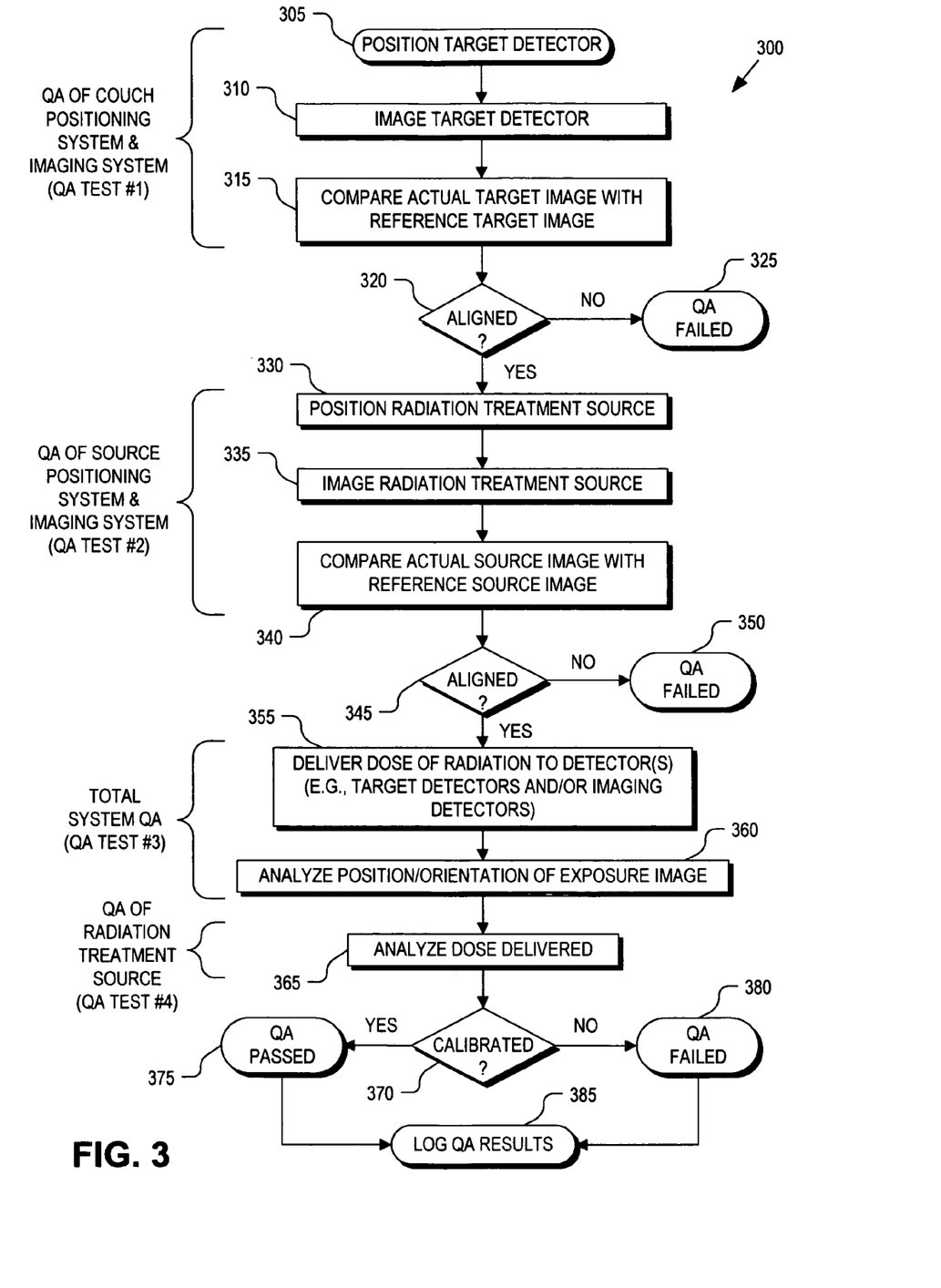
FIG. 3 is a flow chart illustrating a process to implement a unified quality assurance confidence check on a radiation treatment delivery system, in accordance with an embodiment of the invention.

FIG. 3 is a flow chart illustrating a process 300 to implement a unified QA confidence check of a radiation treatment delivery system (e.g., systems 100 or 200), in accordance with an embodiment of the invention. The techniques described may constitute machine-executable instructions embodied within a machine (e.g., computer) readable medium, that when executed by a machine will cause the machine to perform the operations described. The order in which some or all of the process blocks appear in process 300 should not be deemed limiting. Rather, one of ordinary skill in the art having the benefit of the present disclosure will under-stand that some of the process blocks may be executed in a variety of orders not illustrated or even not at all.

In a process block 305, target detector 130 is positioned to a preset target position. In the embodiment illustrated in FIG. 1, positioning target detector 130 includes instructing the couch positioning system to move target detector 130 to the preset target position. Maneuvering target detector 130 may include guiding target detector 130 using the image guidance system visually locking onto tracking fiducials 131. In the embodiment illustrated in FIG. 2, positioning target detector 130 simply includes manually inserting iso-post 205 into a support bracket and placing target detector 130 onto iso-post 205.

Once target detector 130 has been instructed to move to the preset target position, then target detector 130 is imaged to generate a target image 150 of target detector 130 at its actual target position (process block 310). Target image 150 is then transferred to QA processing system 125 and compared against a reference target image 151 (process block 315). In one embodiment, reference target image 151 is an image of target detector 130 taken when target detector 130 is known to have been correctly positioned at the preset target position. By comparing target image 150 against reference target image 151, it can be determined whether the actual target position coincides with the preset target position (decision block 320). Comparing target image 150 to reference target image 151 may include registering features of the two images to one another (e.g., computing image centroids and registering the centroids, registering tracking fiducials 130, or the like).

In the embodiment illustrated in FIG. 2, QA test #1 performed in process blocks 305, 310, and 315 validates alignment of the image guidance system with the fixed reference point. Therefore, if the two images of target detector 130 coincide, the image guidance system must be aligned, within specified error tolerances, with the fixed reference point. However, in the embodiment illustrated in FIG. 1, QA test #1 validates alignment between the couch positioning system and the image guidance system. Therefore, if the two images of target detector 130 coincide, the image guidance system must be aligned, within specified error tolerances, with the preset target position and the couch positioning system must have accurately placed target detector 130 at the preset target position.

If the couch positioning system did not accurately position target detector 130 to the preset target position, then QA validation fails (process block 325). However, if the couch positioning system did accurately position target detector 130 to the preset target position, then process 300 continues to a process block 330. It should be appreciated that process blocks 305, 310, and 315 may be repeated multiple times before an absolute QA failure is determined. Typically, multiple cycles of image acquisition (process block 310) and couch adjustment (process block 305) are needed to achieve alignment. If after several iterations through process blocks 305, 310, and 315, alignment is still unachievable in decision block 320, then a final QA failure is issued in process block 325.

In a process block 330, radiation treatment source 105 is maneuvered to a preset source position. Maneuvering radiation treatment source 105 to the preset source position may include instructing the source positioning system (see FIG. 7) to translate and rotate radiation treatment source 105 to a known preset position.

Once radiation treatment source 105 has been instructed to move to the preset source position, radiation treatment source 105 is imaged to generate a source image 160 of radiation treatment source 105 at its actual source position (process block 335). Source image 150 is then transferred to QA processing system 125 and compared against a reference source image 151 (process block 340). In one embodiment, reference source image 161 is an image of radiation treatment source 105 taken when radiation treatment source 105 is known to have been correctly positioned at the preset source position. In one embodiment, only a portion of radiation treatment source 105 is imaged. For example, snout 107 (also referred to as the collimator housing) may be imaged or other calibration targets strategically positioned on radiation treatment source 105. Radiation treatment source 105 may be imaged by imaging sources 120 generating beam exposure fields onto imaging detectors 115. The portion of radiation treatment source 105 extending into the beam exposure field casts a shadow onto imaging detectors 115, which then may be analyzed for relative position and orientation within the beam exposure field.

By comparing source image 160 against reference source image 161, it can be determined whether the actual source position coincides with the preset source position (decision block 345). Comparing source image 160 to reference source image 161 may include registering features of the two images to one another (e.g., computing image centroids and registering the centroids, registering outlines of the shadows cast, or the like).

In the embodiment illustrated in FIG. 2, QA test #2 performed by process blocks 330, 335, and 340 validates alignment between the source positioning system and the image guidance system. Therefore, if the two images of radiation treatment source 105 coincide, the image guidance system must be aligned, within specified error tolerances, with the preset source position and the source positioning system must have accurately placed radiation treatment source 105 at the preset source position.

If the source positioning system did not accurately position radiation treatment source 105 to the preset source position or the image guidance system is misaligned, then QA validation fails (process block 350). However, if the source positioning system did accurately position radiation treatment source 105 to the preset source position and the image guidance system is aligned, then process 300 continues to a process block 355.

In process block 355, radiation treatment source 105 delivers a dose of radiation to target detector 130 and/or imaging detectors 115 to generate an exposure image. Radiation treatment source 105 delivers the dose of radiation from a preset position (e.g., the preset source position described above or another preset source position). In a process block 360, QA processing system 125 analyzes the exposure image to determine whether the dose of radiation was delivered to an expect position on the detector (e.g., target detector 130 or imaging detectors 115) and with an expected orientation. In one embodiment, QA processing system 125 analyzes the exposure image by comparing the exposure image to a reference exposure image generated by radiation treatment delivery system 100 or 200 known to be correctly calibrated. In one embodiment, comparing the exposure images includes calculating centroids of the exposure image and the reference image and comparing the centroids to determine whether they are concentrically aligned.

QA test #3 performed by process blocks 355 and 360 validates alignment between all three major subsystems: the image guidance system, the couch positioning system, and the source positioning system. If anyone of these subsystems is not aligned with the other two subsystems, then the exposure image generated on the detector (e.g., target detector 130 or imaging detectors 115) will not coincide with the reference exposure image generated during a known good state of radiation treatment delivery system 100 or 200.

In a process block 365, QA processing system 125 further analyzes the exposure image generated in response to delivering a preset dose of radiation to determine whether an expected dose of radiation was actually delivered. If the actual dose delivered matches the expected dose, within error tolerances, then the intensity and dose duration of radiation treatment source 105 is deemed properly calibrated. Test #4 performed by process block 365 validates correct operation of radiation treatment source 105 itself.

If QA tests #1-#4 are all successfully passed (decision block 370), then radiation treatment delivery system 100 or 200 is determined to be correctly aligned and calibrated and QA is passed (process block 375). However, if one or more of tests #1-#4 fails, then at least a portion of radiation treatment delivery system 100 or 200 is determined to be misaligned or incorrectly calibrated and therefore QA fails (process block 380).

In either event, the results/data of QA tests #1-#4 may be logged and saved for future reference and/or tracking purposes (process block 385). In one embodiment, results of QA tests #1-#4 may be transmitted via a network (e.g., Internet) to a central database where a third party can monitor/review the QA procedures and results at various hospitals. The third party may use the QA data to ensure recommended QA procedures are adhered to and/or as feedback information for remedying common problems encountered in the field.

It should be appreciated that the order in which QA tests #1-#4 are performed may be varied from that illustrated in FIG. 3. Furthermore, not all QA tests need be performed each time. For example, QA test #3 may be the sole test performed on a regular basis while the other QA tests are performed less frequently or visa versa.

Figure 4:
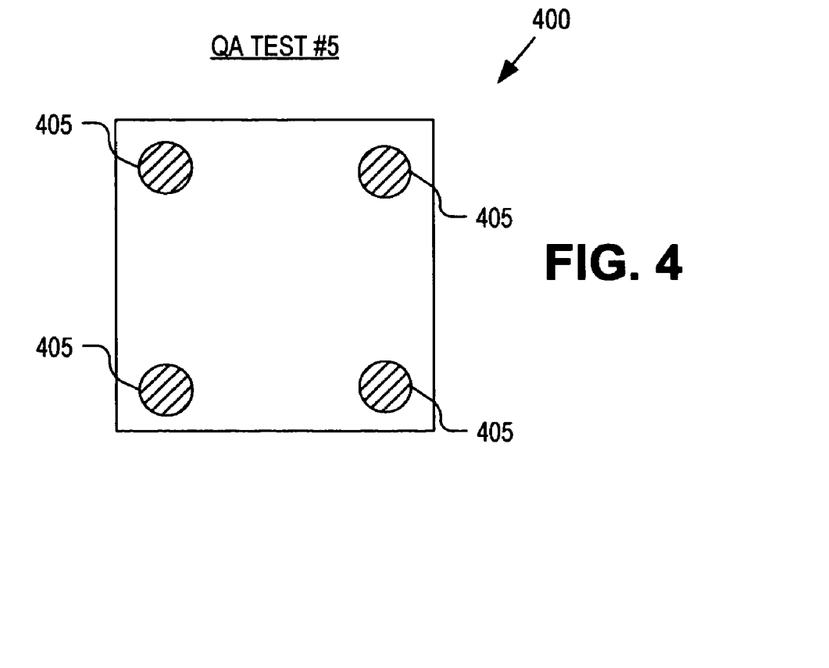
FIG. 4 is a diagram of an exposure image used for verifying alignment of a radiation treatment delivery system, in accordance with an embodiment of the invention.
Figure 5:
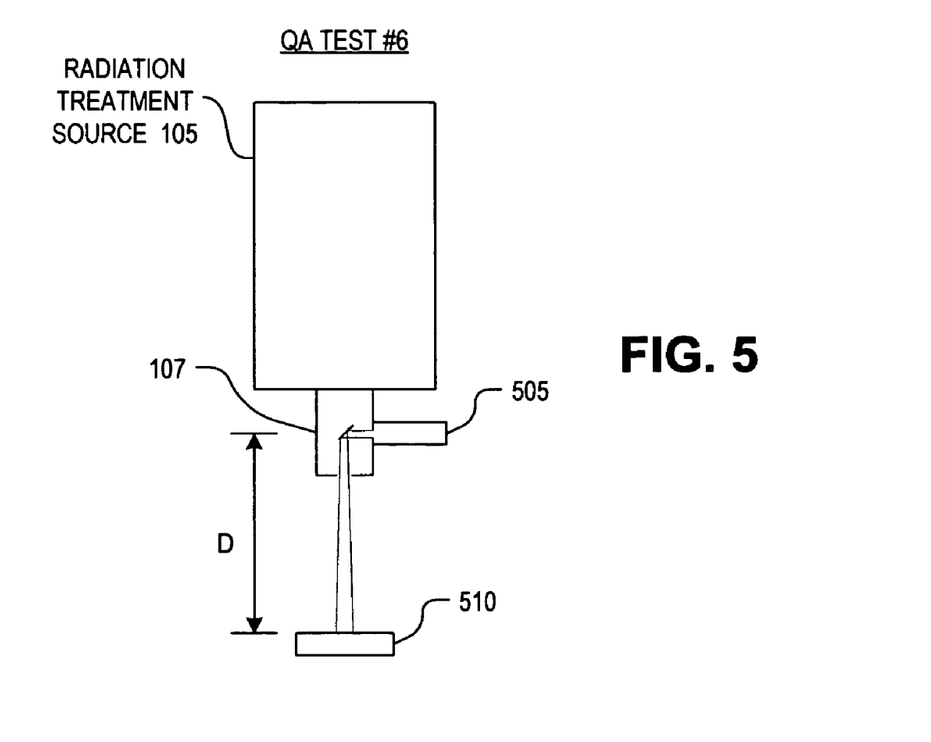
FIG. 5 is a block diagram illustrating a radiation treatment source including an optical source mounted thereon for validating calibration of a source positioning system used to position the radiation treatment source, in accordance with an embodiment of the invention.

FIGS. 4 and 5 illustrate other QA tests that may be performed in addition to QA tests #1-#4 discussed in FIG. 3. FIG. 4 illustrates an example exposure image 400 used for verifying alignment of radiation treatment delivery system 100 (or 200), in accordance with an embodiment of the invention. Radiation treatment source 105 may be maneuvered to a number of preset positions and deliver a dose of radiation at each preset position to either target detector 130 or to one or both of imaging detectors 115. In the illustrated embodiment, radiation treatment source 105 delivers four doses of radiation from preset locations to generate beam exposures 405 within exposure image 400. QA processing system 125 then analyzes exposure image 400 to determine whether beam exposures 405 were produced on the specified detector at the expected locations. Analyzing exposure image 400 may include comparing exposure image 400 to a reference exposure image using image registration techniques. For example, the centroids of beam exposures 405 may be computed and compared to centroids of expected beam exposures within a reference exposure image. Although FIG. 4 illustrates four beam exposures 405, it should be appreciated that more or less beam exposures may be generated in a variety of different patterns.

FIG. 5 is a block diagram illustrating radiation treatment source 105 including an optical source 505 mounted thereon for validating alignment of the source positioning system used to position radiation treatment source 105, in accordance with an embodiment of the invention. In the illustrated embodiment, optical source 505 is mounted to snout 107 to project a test beam therefrom. Optical source 505 may be a laser source, such as a semiconductor laser or otherwise.

An optical detector 510 may be mounted within a room housing radiation treatment delivery system 100 (or 200) or on the system itself. To validate calibration of the source positioning system, the source positioning system is instructed to position radiation treatment source 105 at a preset position pointing at optical detector 510. The test beam is then generated by optical source 505. If the test beam strikes optical detector 510 at the expected location, then the source positioning system may be deemed aligned. In one embodiment, the test beam is further used to measure the distance D between optical detector 510 and optical source 505 as another confidence check on the source positioning system's ability to accurately aim and position radiation treatment source 105. In one embodiment, optical source 505 may be replaced with an ultrasonic sensor or other distance measurement devices.

Figure 6:
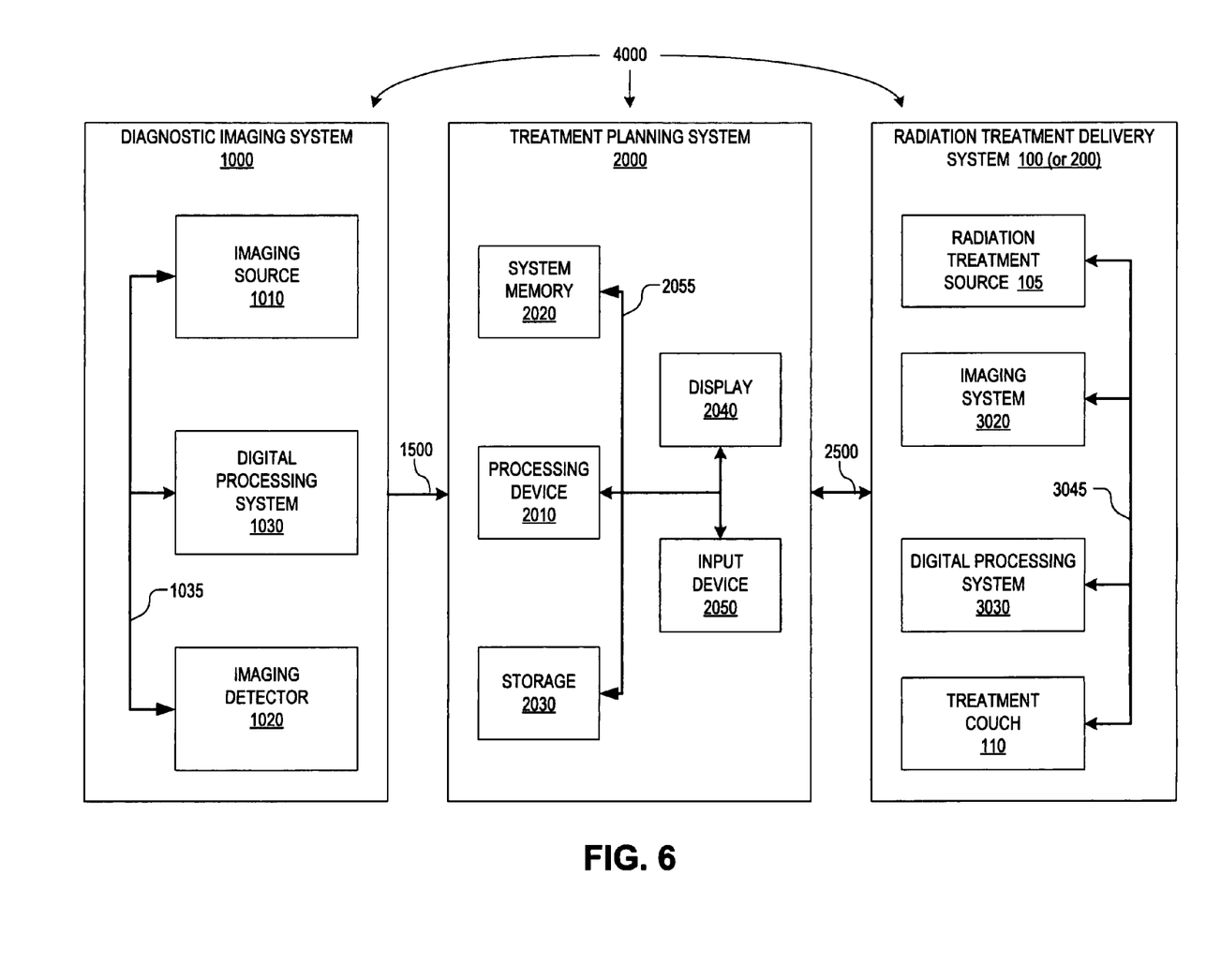
FIG. 6 is a block diagram illustrating a patient treatment system for generating diagnostic images, generating a treatment plan, and delivering the treatment plan, in accordance with an embodiment of the invention.

FIG. 6 is a block diagram illustrating a therapeutic patient treatment system 4000 for generating diagnostic images, generating a treatment plan, and delivering the treatment plan to a patient, in which features of the present invention may be implemented. As described below and illustrated in FIG. 6, systems 4000 may include a diagnostic imaging system 1000, a treatment planning system 2000 and a radiation treatment delivery system 100 (or 200).

Diagnostic imaging system 1000 may be any system capable of producing medical diagnostic images of the VOI within a patient that may be used for subsequent medical diagnosis, treatment planning and/or treatment delivery. For example, diagnostic imaging system 1000 may be a computed tomography ("CT") system, a magnetic resonance imaging ("MRI") system, a positron emission tomography ("PET") system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor ("DSP") or other type of device such as a controller or field programmable gate array ("FPGA"). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network ("LAN") link or a wide area network ("WAN") link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a DSP or other type of device such as a controller or FPGA. Processing device 2010 may be configured to execute instructions for performing treatment planning operations discussed herein.

Treatment planning system 2000 may also include system memory 2020 that may include a random access memory ("RAM"), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory ("ROM") and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube ("CRT") or liquid crystal display ("LCD"), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as radiation treatment delivery system 100 (or 200), so that it may not be necessary to export from the treatment planning system prior to treatment delivery. Treatment planning system 2000 may be linked to radiation treatment delivery system 100 (or 200) via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or radiation treatment delivery system 100 (or 200) may be in decentralized locations such that the systems may be physically remote from each other. Alternatively, any of diagnostic imaging system 1000, treatment planning system 2000 and/or radiation treatment delivery system 100 (or 200) may be integrated with each other in one or more systems.

Radiation treatment delivery system 100 (or 200) includes a therapeutic and/or surgical radiation treatment source 105 to administer a prescribed radiation dose to a target volume in conformance with a treatment plan. Radiation treatment delivery system 100 (or 200) may also include an imaging system 3020 (including imaging sources 120 and detectors 115) to capture inter-treatment images of a patient volume (including the target volume) for registration or correlation with the diagnostic images described above in order to position the patient with respect to the radiation source. Radiation treatment delivery system 100 (or 200) may also include a digital processing system 3030 to control radiation treatment source 105, imaging system 3020, and a patient support device such as a treatment couch 110. Digital processing system 3030 may include one or more general-purpose processors (e.g., a microprocessor), special purpose processor such as a DSP or other type of device such as a controller or FPGA. Digital processing system 3030 may also include other components (not shown) such as memory, storage devices, network adapters and the like. Digital processing system 3030 may be coupled to radiation treatment source 105, imaging system 3020 and treatment couch 110 by a bus 3045 or other type of control and communication interface.

Figure 7:
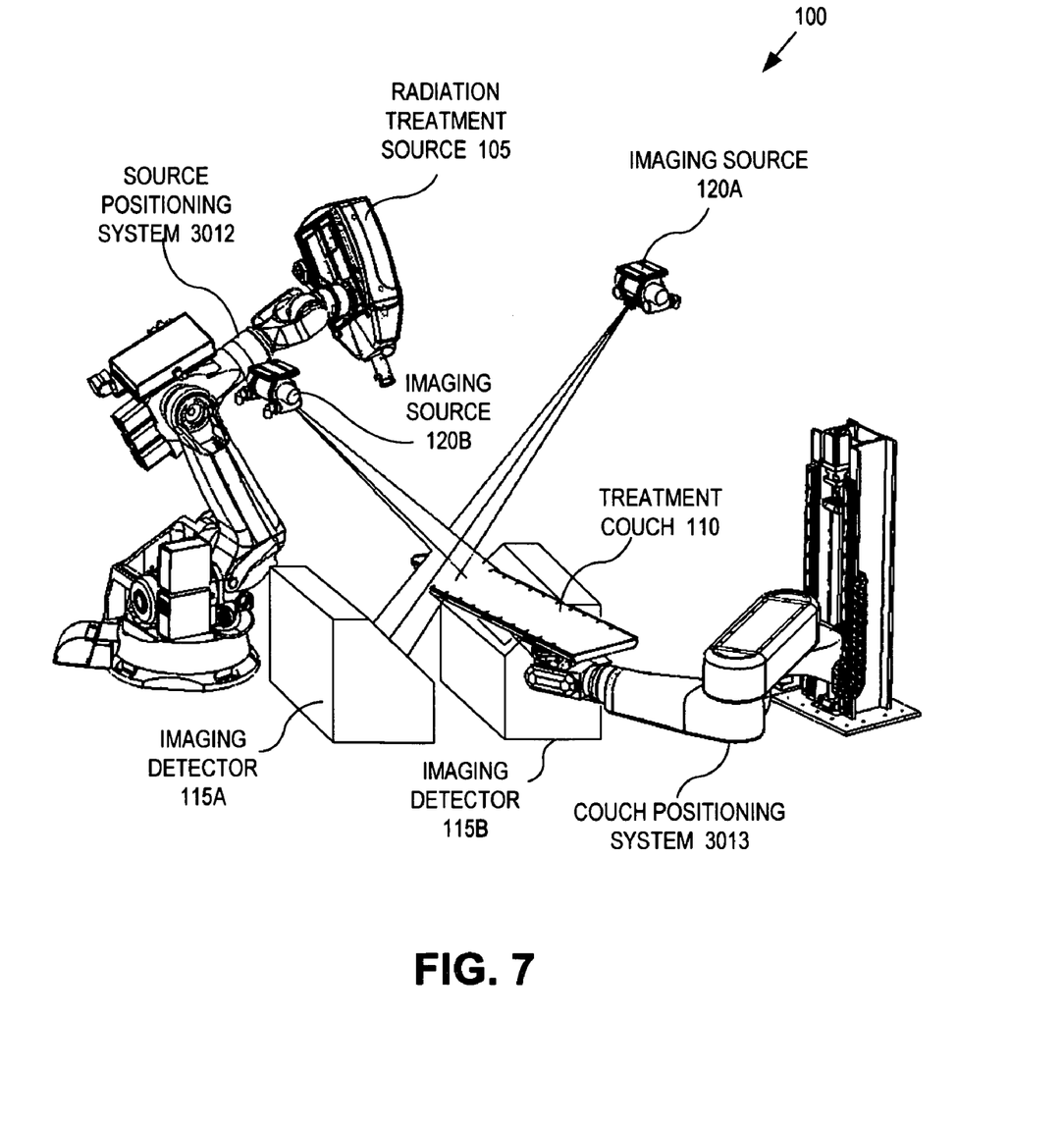
FIG. 7 is a perspective view of a radiation treatment delivery system, in accordance with an embodiment of the invention.

FIG. 7 is a perspective view of a radiation treatment delivery system 100 (or 200), in accordance with an embodiment of the invention. In one embodiment, radiation treatment delivery system 100 (or 200) may be an image-guided, robotic-based radiation treatment system such as the CyberKnife® system developed by Accuray, Inc. of California. In FIG. 7, radiation treatment source 105 may be a linear accelerator ("LINAC") mounted on the end of a source positioning system 3012 (e.g., robotic arm) having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning. With radiation treatment delivery system 100 (or 200), in one embodiment, radiation beams may be delivered according to the treatment plan without fixing the patient to a rigid, external frame to register the intra-operative position of the target volume with the position of the target volume during the pre-operative treatment planning phase.

Imaging system 3020 (see FIG. 6) may be represented by imaging sources 120A and 120B and imaging detectors (imagers) 115A and 115B in FIG. 7. In one embodiment, imaging sources 120A and 120B are X-ray sources. In one embodiment, for example, two imaging sources 120A and 120B may be nominally aligned to project imaging x-ray beams through a patient from two different angular positions (e.g., separated by 90 degrees, 45 degrees, etc.) and aimed through the patient on treatment couch 110 toward respective detectors 115A and 115B. In another embodiment, a single large imager can be used that would be illuminated by each x-ray imaging source.

Alternatively, other numbers and configurations of imaging sources and detectors may be used.

Digital processing system 3030 may implement algorithms to register images obtained from imaging system 3020 with pre-operative treatment planning images in order to align the patient on the treatment couch 110 within the radiation treatment delivery system 100 (or 200), and to precisely position the radiation treatment source 105 with respect to the target volume.

In the illustrated embodiment, treatment couch 110 is coupled to a couch positioning system 3013 (e.g., robotic couch arm) having multiple (e.g., 5 or more) degrees of freedom. Couch positioning system 3013 may have five rotational degrees of freedom and one substantially vertical, linear degree of freedom. Alternatively, couch positioning system 3013 may have six rotational degrees of freedom and one substantially vertical, linear degree of freedom or at least four rotational degrees of freedom. Couch positioning system 3013 may be vertically mounted to a column or wall, or horizontally mounted to pedestal, floor, or ceiling. Alternatively, the treatment couch 110 may be a component of another mechanical mechanism, such as the Axum™ treatment couch developed by Accuray, Inc. of California, or be another type of conventional treatment table known to those of ordinary skill in the art.

Alternatively, radiation treatment delivery system 100 (or 200) may be another type of treatment delivery system, for example, a gantry based (isocentric) intensity modulated radiotherapy ("IMRT") system. In a gantry based system, a therapeutic radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the iso-center to deliver a dose distribution to the target. In IMRT planning, the optimization algorithm selects subsets of the main beam and determines the amount of time that the patient should be exposed to each subset, so that the prescribed dose constraints are best met.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method, comprising:
   instructing an image guided radiation treatment delivery system to move a radiation treatment source to a preset source position, wherein the radiation treatment source is a physical component of the image guided radiation treatment delivery system which includes components for generating a beam of radiation;
   imaging at least a portion of the radiation treatment source after instructing the image guided radiation treatment delivery system to move the radiation treatment source to the preset source position to generate a first image of the portion of the radiation treatment source at an actual source position of the radiation treatment source;
   comparing the first image against a reference source image of the radiation treatment source at the preset source position; and
   determining whether the radiation treatment source correctly achieved the preset source position based at least in part on the comparing.

2. The method of claim 1, wherein instructing the image guided radiation treatment delivery system to move the radiation treatment source to the preset source position comprises instructing a robotic arm supporting the radiation treatment source to move the radiation treatment source to the preset source position.

3. The method of claim 2, wherein imaging the portion of the radiation treatment source comprises imaging the portion of the radiation source with an image guidance system of the image guided radiation treatment delivery system.

4. The method of claim 3, wherein imaging the portion of the radiation treatment source to generate the first image further comprises:
   emitting radiation from an imaging source of the image guidance system; generating a beam exposure field on an imaging detector of the image guidance system; and
   casting a shadow of the portion of the radiation treatment source onto the imaging detector within the beam exposure field.

5. The method of claim 3, further comprising:
   treating an imaging detector of the image guidance system with a dose of radiation from the radiation treatment source to generate an exposure image; and
   comparing the exposure image to a reference exposure image to determine whether the radiation treatment source correctly achieved the preset source position.

6. The method of claim 1, wherein the portion of the radiation treatment source comprises a snout of the radiation treatment source.

7. The method of claim 1, wherein comparing the first image against the reference source image comprises registering the first image against the reference source image.

8. The method of claim 1, wherein determining whether the radiation treatment source correctly achieved the preset source position comprises determining whether the actual source position is equal to the preset source position within a specified error tolerance.

9. The method of claim 1, further comprising:
   instructing a positioning system of the image guided radiation treatment delivery system to position a target detector to a preset target position;
   imaging the target detector after instructing the positioning system to move to the preset target position to generate a second image of the target detector at an actual target position of the target detector;
   comparing the second image against a reference target image at the preset target position; and determining whether the positioning system correctly achieved the preset target position.

10. The method of claim 9 wherein the target detector is positioned on a treatment couch of the image guided radiation treatment delivery system, the treatment couch for supporting patients during delivery of a treatment plan.

11. The method of claim 9 wherein the target detector includes tracking fiducials for use by an image guidance system of the image guided radiation treatment delivery system to position the target detector.

12. The method of claim 9, further comprising:
delivering a dose of radiation to the target detector with the radiation treatment source after instructing the positioning system to position the target detector to the preset target position to generate an exposure image;
analyzing the exposure image to determine whether the dose of radiation was delivered to an expected position; and
determining whether the image guided radiation treatment delivery system is calibrated.

13. The method of claim 12, further comprising analyzing the exposure image to determine whether an expected dose of radiation was delivered.

14. The method of claim 1, further comprising:
delivering a dose of radiation to a target detector positioned at a reference point to generate an exposure image; and
analyzing a position of the exposure image on the target detector to determine whether the image guided radiation treatment delivery system is calibrated.

15. The method of claim 1, further comprising:
emitting an optical signal from an optical source mounted to the radiation treatment source after instructing the radiation treatment source to move to the preset position;
monitoring an optical detector positioned at a known position to determine whether the optical signal is received; and
determining whether the radiation treatment source correctly achieved the preset position based on a response from the optical detector.

16. The method of claim 1, further comprising:
logging quality assurance data after determining whether the radiation treatment source correctly achieved the preset position; and
providing the quality assurance data for remote access via the Internet.

17. A radiation treatment delivery system, comprising:
a source positioning system coupled to robotically position a radiation treatment source, wherein the radiation treatment source is a physical component of the radiation treatment delivery system which includes components for generating a beam of radiation;
an imaging system positioned to image at least a portion of the radiation treatment source; and
a processing system communicatively coupled to the source positioning system and the imaging system, the control system including a machine-accessible medium that provides instructions that, if executed will cause the processing system to perform operations comprising:
instructing the source positioning system to move the radiation treatment source to a preset source position;
instructing the imaging system to image at least a portion of the radiation treatment source to generate a first image of the portion of the radiation treatment source at an actual source position of the radiation treatment source; and
determining whether the radiation treatment source correctly achieved the preset source position based at least in part on comparing the first image against a reference source image of the radiation treatment source at the preset source position.

18. The radiation treatment delivery system of claim 17 wherein the machine-accessible medium further providing instructions that, if executed will cause the processing system to perform further operations, comprising:
instructing the radiation treatment source to deliver a dose of radiation to a detector from the actual source position to generate an exposure image; and
comparing the exposure image to a reference exposure image to determine whether the radiation treatment source correctly achieved the preset source position.

19. The radiation treatment delivery system of claim 17 further comprising a couch positioning system coupled to position a treatment couch, and wherein the machine-accessible medium further providing instructions that, if executed will cause the processing system to perform further operations, comprising:
instructing the couch positioning system to position a target detector to a preset target position;
instructing the imaging system to image the target detector to generate a second image of the target detector at an actual target position of the target detector; and
determining whether the couch positioning system correctly achieved the preset target position based at least in part on comparing the second image against a reference target image of the target detected at the preset target position.

20. The radiation treatment delivery system of claim 19 wherein the machine-accessible medium further providing instructions that, if executed will cause the processing system to perform further operations, comprising:
instructing the radiation treatment source to deliver a dose of radiation to the target detector to generate an exposure image;
analyzing the exposure image to determine whether the dose of radiation was delivered to an expected position; and
determining whether the radiation treatment delivery system is calibrated.

21. A radiation treatment delivery system, comprising:
means for instructing an image guided radiation treatment delivery system to move a radiation treatment source to a preset source position, wherein the radiation treatment source is a physical component of the radiation treatment delivery system which includes components for generating a beam of radiation;
means for imaging at least a portion of the radiation treatment source after instructing the image guided radiation treatment delivery system to move the radiation treatment source to the preset source position to generate a first image of the portion of the radiation treatment source at an actual source position of the radiation treatment source;
means for comparing the first image against a reference source image of the radiation treatment source at the preset source position; and
means for determining whether the radiation treatment source correctly achieved the preset source position based at least in part on the means for comparing.

22. The radiation treatment delivery system of claim 21, wherein the means for imaging the portion of the radiation treatment source to generate the first image comprises:
means for emitting radiation for imaging;
means for generating a beam exposure field in response to the means for emitting radiation; and means for casting a shadow of the portion of the radiation treatment source onto the means for generating a beam exposure field.

23. The radiation treatment delivery system of claim 21, further comprising:
   means for instructing a positioning system of the image guided radiation treatment delivery system to position a target detector to a preset target position;
   means for imaging the target detector after instructing the positioning system to move to the preset target position to generate a second image of the target detector at an actual target position of the target detector;
   means for comparing the second image against a reference target image at the preset target position; and
   means for determining whether the positioning system correctly achieved the preset target position.

24. The radiation treatment delivery system of claim 23, further comprising:
   means for delivering a dose of radiation to the target detector with the radiation treatment source after instructing the positioning system to position the target detector to the preset target position to generate an exposure image;
   means for analyzing the exposure image to determine whether the dose of radiation was delivered to an expected position; and
   means for determining whether the image guided radiation treatment delivery system is calibrated.

25. The radiation treatment delivery system of claim 24, further comprising means for analyzing the exposure image to determine whether an expected dose of radiation was delivered.

26. The radiation treatment delivery system of claim 21, further comprising:
   means for delivering a dose of radiation to a target detector positioned at a reference point; and
   means for analyzing the dose of radiation to determine whether the image guided radiation treatment delivery system is calibrated.

* * * * *